United States Patent [19]

Urata et al.

[11] Patent Number: 5,410,887
[45] Date of Patent: May 2, 1995

[54] APPARATUS FOR DETECTING COMPOSITION OF REFRIGERANT AND METHOD THEREFOR

[75] Inventors: Kazumoto Urata, Shizuoka; Kensaku Oguni, Shimizu; Kyuhei Ishibane, Shimizu; Naoto Katsumata, Shimizu, all of Japan

[73] Assignee: Hitachi, Ltd., Tokyo, Japan

[21] Appl. No.: 129,351

[22] Filed: Sep. 30, 1993

[30] Foreign Application Priority Data

Oct. 1, 1992 [JP] Japan .................. 4-263385

[51] Int. Cl.⁶ .................................. F25B 49/02
[52] U.S. Cl. .................................. 62/129; 62/114
[58] Field of Search ............. 62/114, 126, 129, 125, 62/127, 149, 174

[56] References Cited

U.S. PATENT DOCUMENTS

| | | | |
|---|---|---|---|
| 5,009,076 | 4/1991 | Winslow | 62/129 |
| 5,152,152 | 10/1992 | Brickner et al. | 62/126 |
| 5,158,747 | 10/1992 | Manz et al. | 62/127 X |
| 5,239,865 | 8/1993 | Salzer et al. | 62/129 X |

FOREIGN PATENT DOCUMENTS

| | | |
|---|---|---|
| 59-129366 | 7/1984 | Japan . |
| 61-138058 | 6/1986 | Japan . |
| 1-256765 | 10/1989 | Japan . |

*Primary Examiner*—Harry B. Tanner
*Attorney, Agent, or Firm*—Antonelli, Terry, Stout & Kraus

[57] ABSTRACT

A mixed-refrigerant comprising two or more types of refrigerants having different boiling points is enclosed in a refrigerating cycle and a capacitance sensor is used as a device for detecting a composition of the mixed-refrigerant. The electrostatic capacitance sensor is disposed in an evaporation portion of the refrigerating cycle. The refrigerating cycle has a refrigerant composition calculating device for calculating a composition of the refrigerant in the refrigerating cycle in accordance with an output signal from the capacitance sensor and an adequate composition judging device for judging whether or not the composition of the mixed-refrigerant circulating in the refrigerating cycle is in an adequate state in accordance with an output signal from the refrigerant composition calculating device.

2 Claims, 11 Drawing Sheets

APPARATUS FOR DETECTING COMPOSITION OF REFRIGERANT AND METHOD THEREFOR

BACKGROUND OF THE INVENTION

The present invention relates to an apparatus and a method of detecting composition of a refrigerant in a refrigerating cycle, and more particularly to an apparatus and a method of detecting composition of mixed-refrigerant circulating in a refrigerating cycle in which the mixed-refrigerant is sealingly filled.

Various methods have been proposed to detect composition of a mixed-refrigerant sealingly filled in a refrigerating cycle.

For example, a heat pump apparatus disclosed in Japanese Patent Unexamined Publication No. 61-138058 comprises a temperature detection portion and a pressure detection portion disposed to detect the temperature and the pressure in the apparatus when the mixed-refrigerant in the apparatus has reached equilibrium by allowing to stand the apparatus for a while after the operation of the heat pump apparatus has been stopped. The method employs a relational graph between temperature and a saturated pressure of the refrigerant which is determined by an internal capacity of the heat pump apparatus, the kinds of the component refrigerants of the mixed-refrigerant, an initial mixture ratio of the mixed-refrigerant and an initial quantity of the enclosed mixed-refrigerant. Then, a saturated pressure at a temperature detected by the temperature detecting portion is calculated. Then, a difference between the saturated pressure and a pressure detected by the pressure detecting portion is calculated to judge a deviation from an initial state of the refrigerant composition. If the deviation is larger than a predetermined value, the mixed-refrigerant is supplemented.

Another prior art for detecting the refrigerant composition has been disclosed in Japanese Patent Unexamined Publication No. 59-129366. In this case, a concentration sensor having a pair of electrodes disposed to face each other with a space therebetween and located in a high-pressure liquid passage arranged from a condenser to an expansion valve are used to detect a capacitance of a flowing refrigerant so that the concentration of the circulating mixed-refrigerant is detected.

Another structure has been prepared in which the composition change in the refrigerating cycle due to leakage of the refrigerant is detected and the result of the detection is fed back to control of the refrigerating cycle. For example, a refrigerating cycle control apparatus for a vehicle disclosed in Japanese Patent Unexamined Publication No. 1-256765 has a refrigerating cycle and opening-degree control means for controlling the degree of opening of expansion valve means so as to make it adequate the degree of superheat of the refrigerant flowing from evaporation means to compression means, and the refrigerating cycle controlling apparatus comprises detection means for detecting a temperature and a pressure of a liquid-phase component flowing from gas-liquid separating means to the expansion valve means, composition ratio judging means for judging the composition in the refrigerating cycle in accordance with the result of detection performed by the detection means, and adjusting means for adjusting a target value of the degree of superheat of the refrigerant to a somewhat larger value in accordance with the result of the judgement. If the composition of the mixed-refrigerant is changed when the mixed-refrigerant outwardly leaks for some reason, the temperature and the pressure of the refrigerant, that are changed in accordance with the foregoing change, are detected from the liquid phase component of the gas-liquid separating means, the composition of the mixed-refrigerant is judged by the composition ratio judging means, the target value of the degree of superheat of the refrigerant is adjusted to a larger value in accordance with the result of the judgement, and the degree of superheat of the refrigerant is controlled by the opening degree control means. Therefore, the cooling performance of the mixed-refrigerant can always be maintained regardless of the leakage of the mixed-refrigerant.

However, each of the foregoing structures detecting the composition of the mixed-refrigerant enclosed in the refrigerating cycle and the refrigerating cycle arranged in such a manner that the composition of the refrigerant is detected and the result of the detection is fed back to control the operation of the refrigerating cycle needs that the refrigerating cycle is stable. Consideration has not been taken to a case where the refrigerating cycle is unstable.

That is, the structure disclosed in Japanese Patent Unexamined Publication No. 61-138051 takes a long time for the refrigerating cycle to be equilibrated, so that the time period during which the refrigerant composition can be detected becomes long. If the refrigerant composition is changed, the operation control must be changed in accordance with the change of the composition. However, the refrigerant composition detected when the operation of the refrigerating cycle is stopped differs from the refrigerant composition in operation of the refrigerating cycle, so that it is not possible to effect a suitable operation thereof. Further, a separate-type air conditioner in which an indoor unit and an outdoor unit are disposed at different places encounters a fact that the temperature conditions for the indoor unit and those for the outdoor unit are different from each other. Therefore, the mixed-refrigerant in the refrigerating cycle cannot be brought to the gas-liquid equilibrium state. As a result, there is a possibility to detect a refrigerant composition different from the actual refrigerant composition.

In the structure disclosed in Japanese Patent Unexamined Publication No. 59-129366, the high pressure passage formed from an Outlet port of the condenser to the expansion valve cannot always be made the superheat liquid state at starting of the refrigerating cycle due to the temperature condition of the place to be air-conditioned or the leakage of the refrigerant or the like. In a case where a gas-liquid phase state is realized, capacitance varies in dependent upon wetness of the refrigerant. Hence, there is a possibility to detect refrigerant composition different from the actual composition of the refrigerant circulating in the refrigerating cycle.

In the structure disclosed in Japanese Patent Unexamined Publication No. 1-256765, because the gas-liquid separating means to detect the refrigerant composition is used, the cost of the refrigerant detection sensor is increased. Further, the level change of the liquid reserved in the gas-liquid separator changes the composition of the refrigerant circulating in the refrigerating cycle. As a result, there arises a problem that the refrigerating cycle becomes unstable.

SUMMARY OF THE INVENTION

An object of the present invention is to provide an apparatus and a method capable of always and surely detecting the composition-of a mixed-refrigerant employed as a cooling fluid in a refrigerating cycle even if the mixed-refrigerant leaks out or retained in the refrigerating cycle.

In order to achieve the foregoing object, according to a first aspect of the present invention, there is provided a refrigerant composition detecting apparatus for detecting the composition of a mixed-refrigerant comprising two or more types of refrigerants having different boiling points and enclosed in a refrigerating cycle having a compressor, a condenser, a pressure reducing device and an evaporator, the refrigerant composition detecting apparatus comprising: a capacitance sensor serving as means for detecting the composition of the mixed-refrigerant and disposed in an evaporation portion of the refrigerating cycle; a refrigerant composition calculating portion for calculating the refrigerant composition in the refrigerating cycle in accordance with an output signal from the capacitance sensor; and an adequate composition judging portion for judging whether or not the composition of the mixed-refrigerant circulating in the refrigerating cycle is in an adequate state in accordance with an output signal from the refrigerant composition calculating portion.

According to a second aspect of the invention, there is provided a refrigerant composition detecting apparatus having temperature detecting means and pressure detecting means serving as means for detecting the composition of a mixed-refrigerant comprising of a high-boiling-point refrigerant and a low-boiling-point refrigerant enclosed in a refrigerating cycle having a compressor, a condenser, a pressure reducing device and an evaporator, wherein the temperature detecting means and the pressure detecting means are disposed in a gas-liquid phase portion of the refrigerating cycle, the refrigerant composition detecting apparatus comprising: a saturated refrigerant composition judging portion for judging a saturated composition of the mixed-refrigerant circulating in the refrigerating cycle in a saturated condition in accordance with output signals from the temperature detecting means and the pressure detecting means; a memory portion for storing an output signal from the saturated refrigerant composition judging portion at a time when the refrigerant is adequately enclosed; a composition-change calculating portion for calculating a difference between a composition value realized after a predetermined time has passed and obtained from the saturated refrigerant composition judging portion and a composition value stored in the memory portion and realized at the time of adequate enclosure; and an adequate composition judging portion for judging whether or not the composition of the mixed-refrigerant circulating in the refrigerating cycle is in an adequate state in accordance with an output signal from the composition change calculating portion.

According to a third aspect of the invention, there is provided a refrigerant composition detecting apparatus in which a mixed-refrigerant comprising a high-boiling-point refrigerant and a low-boiling-point refrigerant is enclosed in a refrigerating cycle including a compressor, a condenser, a liquid receptor, a pressure reducing device and an evaporator and which has temperature detecting means and pressure detecting means to serve as means for detecting the composition of the mixed-refrigerant, wherein the temperature detecting means and the pressure detecting means are disposed in a liquid receptor, the refrigerant composition detecting apparatus comprising: a saturated refrigerant composition judging portion for judging a saturated composition of the mixed-refrigerant circulating in the refrigerating cycle in accordance with output signals from the temperature detecting means and the pressure detecting means during an operation of the refrigerating cycle; a memory portion for storing an output signal from the saturated refrigerant composition judging portion at a time when the refrigerant is adequately enclosed; a composition-change calculating portion that detects the composition value supplied from the saturate refrigerant composition judging portion at predetermined time intervals to calculate the difference from the composition value stored in the memory portion at the time when the refrigerant is adequately enclosed; and an adequate composition judging portion for judging whether or not the composition of the mixed-refrigerant circulating in the refrigerating cycle is in an adequate state in accordance with an output signal from the composition change calculating portion.

According to a fourth aspect of the invention, there is provided a refrigerant composition detecting apparatus in which a mixed-refrigerant comprising a high-boiling-point refrigerant and a low-boiling-point refrigerant is enclosed in a refrigerating cycle including a compressor, a condenses, a liquid receptor, a pressure reducing device and an evaporator and which has temperature detecting means and pressure detecting means to serve as means for detecting the composition of the mixed-refrigerant, the refrigerant composition detecting apparatus comprising: liquid level detecting means for detecting a liquid level in the liquid receptor; liquid level adjustment means for adjusting the liquid level in the liquid receptor in accordance with an output signal from the liquid level detecting means; the temperature detecting means and the pressure detecting means being disposed in an outlet pipe from the liquid receptor, a saturated liquid refrigerant composition calculating portion for calculating the composition of a saturated solution of the mixed-refrigerant circulating in the refrigerating cycle in accordance with output signals from the temperature detecting means and the pressure detecting means; and an adequate composition judging portion for judging whether or not the composition of the mixed-refrigerant circulating in the refrigerating cycle is in an adequate state in accordance with an output signal from the saturated liquid refrigerant composition calculating portion.

According to a fifth aspect of the invention, there is provided a refrigerant composition detection apparatus having temperature detecting means and pressure detecting means for detecting the composition of a mixed-refrigerant comprising a high-boiling-point refrigerant and a low-boiling-point refrigerant in a refrigerating cycle, wherein both of the temperature detecting means and the pressure detecting means are disposed between an evaporator and a compressor, the refrigerant composition detecting apparatus comprising: control means for controlling an operation of the refrigerating cycle so that the refrigerant flowing in the temperature and pressure detecting means becomes in a wet condition; refrigerant composition calculating means for calculating the composition of the mixed-refrigerant circulating in the refrigerating cycle in accordance with signals transmitted from the temperature detecting means and the pressure detecting means; and adequate composition judging means for judging whether or not the composition of the mixed-refrigerant circulating in the refrigerating cycle is in an adequate state in accordance with an output signal from the refrigerant composition calculating means.

According to a sixth aspect of the invention, there is provided a method of detecting the refrigerant composition in a refrigerating cycle into which a mixed-refrigerant composed of two refrigerants having different boiling points is enclosed by using a capacitance sensor, the method comprising the steps of: detecting a capacitance value of the mixed-refrigerant in an evaporation portion of the refrigerating cycle by using the capacitance sensor; calculating the composition of at least one of the refrigerants in the refrigerating cycle from the detected capacitance value; comparing the calculated composition of at least one of the refrigerants and an initial composition thereof; and transmitting a signal denoting leakage of the mixed-refrigerant when the obtained difference is larger than a predetermined value.

As described above, the refrigerant composition detecting apparatus according to the first aspect of the present invention has the arrangement that the capacitance sensor serving as means for detecting the composition of the mixed-refrigerant is disposed in the evaporating portion of the refrigerating cycle. Therefore, the composition of the refrigerant can always and stably be detected regardless of the operational state of the refrigerating cycle.

The refrigerant composition detecting apparatus according to the second aspect of the present invention has the arrangement that the temperature detecting means and the pressure detecting means already provided for the conventional refrigerating cycle are used to calculate the saturated refrigerant composition from the temperature and the pressure of the gas-liquid phase portion of the mixed-refrigerant circulating in the refrigerating cycle, and the result of the calculation is subjected to a comparison with the saturated refrigerant composition calculated at a time when it is correctly enclosed to judge whether or not the refrigerant composition in the refrigerating cycle is in an adequate state. Therefore, whether or not the abnormal refrigerant composition has been realized due to the refrigerant leakage can easily be judged. Further, the arrangement that composition is detected by using the detecting means provided for the conventional refrigerating cycle enables the sensor serving as the composition detecting means to be omitted from the structure. Therefore, the cost can be reduced and the control circuit can be simplified.

The refrigerant composition detecting apparatus according to the third aspect of the present invention has the arrangement that the temperature detecting means and the pressure detecting means for detecting the refrigerant composition are provided for the liquid receptor, and the comparison is, in response to the output signal from the temperature and pressure detecting means during the operation of the refrigerating cycle, made between the composition value of the mixed-refrigerant circulating in the refrigerating cycle in the saturated state and the composition value at a time when it is correctly enclosed in the saturated state to judge whether or not the composition of the refrigerant in the refrigerating cycle is in an adequate state. Since the liquid refrigerant and the gas refrigerant in the liquid receptor are substantially in the saturated state, the refrigerant composition can be easily and surely detected from the temperature and the pressure.

The refrigerant composition detecting apparatus according to the fourth aspect of the present invention has the arrangement that the liquid level in the liquid receptor is controlled by the liquid level adjustment means in accordance with the output signal from the liquid level detecting means, which detects the liquid level of the liquid receptor. Further, the temperature detecting means and the pressure detecting means serving as the refrigerant composition detecting means are disposed in the outlet pipe of the liquid receptor to detect the composition value of the saturated liquid state mixed-refrigerant circulating in the refrigerating cycle in response to the output signal from the temperature and the pressure detecting means during the operation of the refrigerating cycle. The detected result is subjected to a comparison with the composition value at a time when it is correctly enclosed to judge whether or not the refrigerant composition in the refrigerating cycle is in the adequate state. By making the liquid level in the liquid receptor to be always constant, the composition of the refrigerant circulating in the refrigerating cycle can be made constant if no refrigerant leakage takes place and the refrigerant at the outlet of the liquid receptor is in the saturated liquid state. Therefore, the enclosed refrigerant has the liquid refrigerant composition if no refrigerant leakage takes place. As a result, the refrigerant composition can surely be detected. Further, the arrangement, that the liquid level in the liquid receptor is made constant, improves the stability of the refrigerating cycle.

The refrigerant composition detecting apparatus according to the fifth aspect of the present invention has the arrangement that the temperature detecting means and the pressure detecting means, which are the means for detecting the refrigerant composition, are disposed between the evaporator and the compressor. An operation of the refrigerating cycle is controlled so that the refrigerant-flowing in the temperature and pressure detecting means becomes in a wet condition. Further, the saturated composition of the mixed-refrigerant circulating in the refrigerating cycle is detected in accordance with the output signals from the temperature detecting means and the pressure detecting means. The detected result is subjected to a comparison with the saturated composition at a time when it is correctly enclosed to judge whether or not the refrigerant composition is in the adequate state. Since the refrigerant in the portion, in which the temperature detecting means and the pressure detecting means are disposed, is so controlled as to be always the gas-liquid phase, the saturated composition can be surely detected. Therefore, whether or not the adequate composition is realized can be surely recognized. Since the temperature detecting means and the pressure detecting means for detecting the refrigerant composition can also be used to control the operation of the refrigerating cycle, the number of the sensor devices can be decreased.

The refrigerant composition detecting method according to the sixth aspect of the present invention has the steps of detecting a capacitance value of the mixed-refrigerant in an evaporation portion of said refrigerating cycle by using the capacitance sensor; calculating the composition of at least one of the refrigerants in said refrigerating cycle from the detected capacitance value; comparing the calculated composition of at least one of the refrigerants and an initial composition of thereof; and transmitting a signal denoting leakage of said mixed-refrigerant when the obtained difference is larger than a predetermined value. Therefore, the optimum quantity of the enclosed refrigerant can be always confirmed, and the realized stable refrigerant composition enables the operation to be performed stably.

DESCRIPTION OF THE PREFERRED EMBODIMENTS

Preferred embodiments of the present invention will now be described with reference to the drawings.

Figure 1:
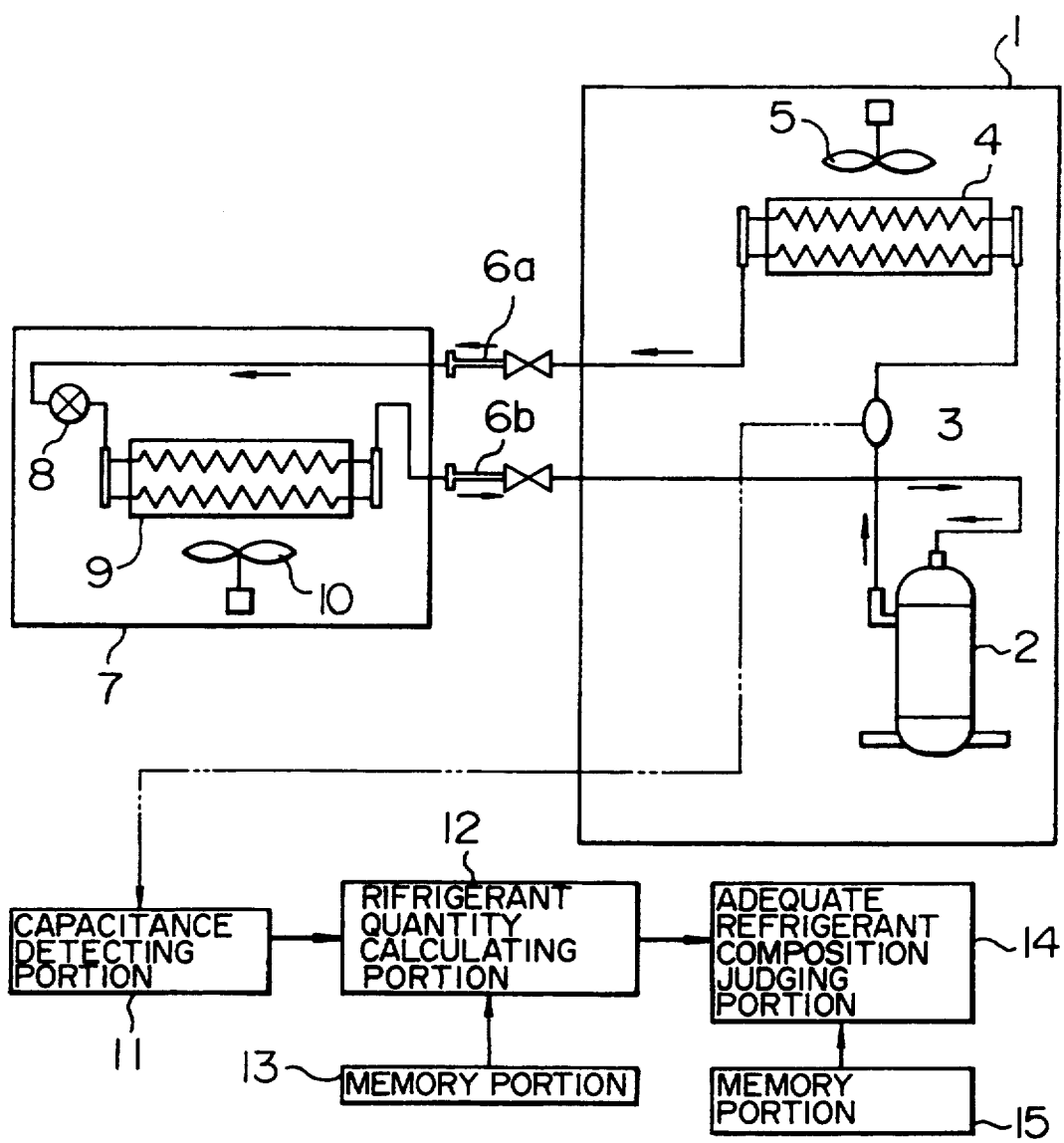
FIG. 1 is a structural view of a refrigerating cycle having refrigerant composition detecting means according to a first embodiment of a refrigerant composition detecting apparatus of the present invention.

FIG. 1 is a structural view which illustrates a refrigerating cycle according to a first embodiment of the present invention. Referring to FIG. 1, reference numeral 1 represents an outdoor unit comprising a compressor 2 for compressing a mixed-refrigerant, a capacitance sensor 3 serving as means for detecting composition of the mixed-refrigerant, a condensing-side heat-exchanger 4 for condensing the mixed-refrigerant and a fan 5 for the heat-exchanger 4 for supplying air that causes heat exchange with the condensing-side heat-exchanger 4. Reference numeral 7 represents an indoor unit comprising an expansion valve 8 for lowering the pressure of the high pressurized mixed-refrigerant which has been condensed and liquefied, an evaporating-side heat-exchanger 9 for evaporating the mixed-refrigerant and a fan 10 for the evaporating,side heat-exchanger 9 for supplying air that causes heat exchange with the evaporating-side heat-exchanger 9. The outdoor unit 1 and the indoor unit 7 are connected to each other by connection pipes 6a and 6b so that the refrigerant can be circulated through the two units. The refrigerating cycle is constituted by sequentially and circularly connecting the compressor 2, the condensing-side heat-exchanger 4, the expansion valve 8 and the evaporating-side heat-exchanger 9. The outdoor unit 1 includes a capacitance detecting portion 11 that receives an output signal from the capacitance sensor 3 to detect a capacitance value. The outdoor unit 1 further includes a refrigerant composition calculating portion 12 for calculating the composition of the mixed-refrigerant circulating in the refrigerating cycle in accordance with the output signal from the capacitance detecting portion 11 and a value stored in a memory portion 13 in which a relationship between the compositions of the refrigerant and the capacitance values is stored. The outdoor unit 1 further includes an adequate refrigerant composition judging portion 14 for judging whether or not the composition of the mixed-refrigerant in the refrigerating cycle is adequate composition in accordance with the output signal from the refrigerant composition calculating portion 12 and a value stored in a memory portion 15 in which a value of the composition of the refrigerant when initially enclosed in the cycle is stored. The foregoing portions included in the outdoor unit 1 are connected to one another by signal lines. It should be noted that arrows shown in FIG. 1 designate the directions of the flow of the mixed-refrigerant in the refrigerating cycle.

Figure 2:
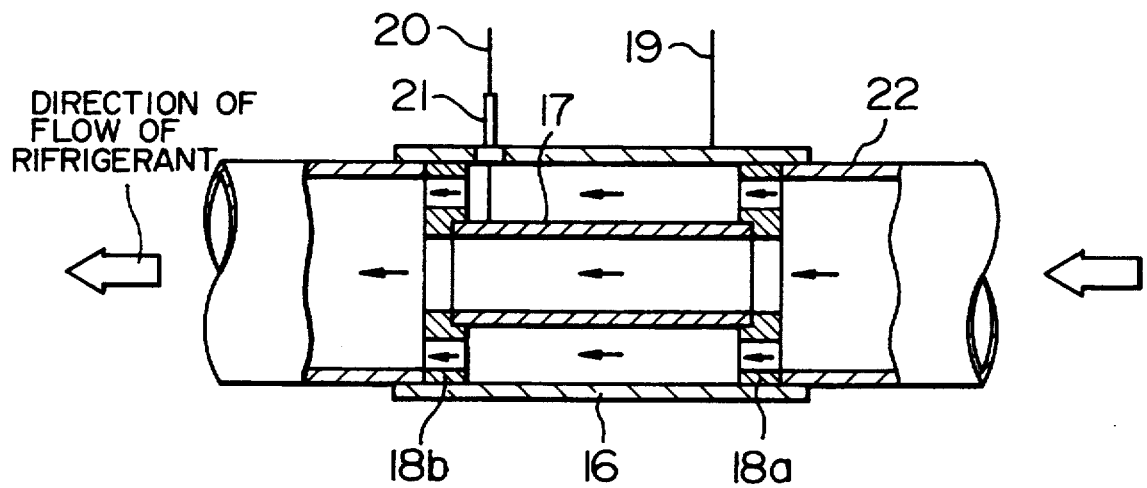
FIG. 2 is a cross sectional view of a capacitance type composition detecting sensor serving as an embodiment of composition detecting means for use in the refrigerant composition detecting apparatus according to the present invention.

An example of a structure of the capacitance sensor 3 for detecting the composition of the mixed-refrigerant will now be described. FIG. 2 is a cross sectional view which illustrates an embodiment of the capacitance sensor 3 for use as the means for detecting the composition of the mixed-refrigerant. Referring to FIG. 2, reference numeral 16 represents an outer tubular electrode and 17 represents an inner tubular electrode each of which is a hollow tube. The inner tubular electrode 17 is, by stopper 18a and 18b having a circular groove at the two ends of the inner tubular electrode 17, fixed coaxially with the outer tubular electrode 16, the stoppers 18a and 18b each having a size substantially the same as an inner diameter of the outer tubular electrode 16. The stoppers 18a and 18b are fixed by refrigerant introduction pipes 22 each having an outer diameter substantially the same as the inner diameter of the outer tubular electrode 16. The refrigerant introduction pipes 22 are fixed to the outer tubular electrode 16. As a result, the inner tubular electrode 17 is rigidly fixed coaxially with the outer tubular electrode 16. In order to detect the capacitance value, an outer-tubular-electrode signal line 19 and an inner-tubular-electrode signal line 20 are connected to the outer tubular electrode 16 and the inner tubular electrode 17. Further, a signal-line outlet pipe 21 (for example, a hermetic terminal) for letting out the inner-tubular-electrode signal line 20 to an outside of the outer tubular electrode 16 and preventing outward leakage of the refrigerant is disposed to surround the inner-tubular-electrode signal line 20. Each of the stoppers 18a and 18b has a penetration passage each having a diameter smaller than the inner diameter of the inner tubular electrode 17 at a center thereof and one or more refrigerant passage at a position between the inner tubular electrode 17 and the outer tubular electrode 16 in order to prevent the interruption of flow of the mixed-refrigerant through the stoppers 18a and 18b.

Figure 3:
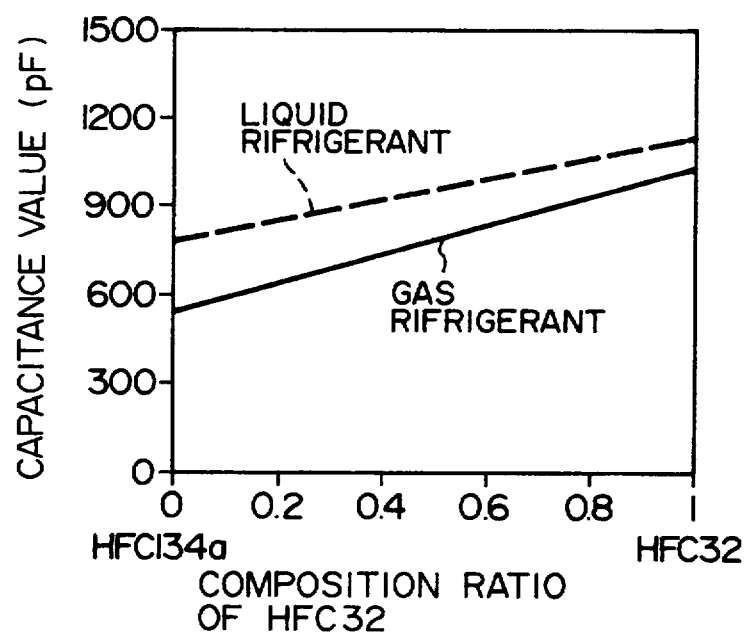
FIG. 3 is a graph showing a relationship between the capacitance values and the compositions of the mixed-refrigerant realized in the capacitance type composition detecting sensor shown in FIG. 2.

A principle of detecting the composition of the mixed-refrigerant by using the capacitance sensor 3 will now be described. FIG. 3 is a graph showing a relationship between the compositions of the refrigerant and the capacitance values realized when the capacitance sensor is used. FIG. 3 shows values when a mixture refrigerant composed of high boiling point refrigerant HFC134a and low boiling point refrigerant HFC32 is used in two cases consisting of a case where it is, in the form of a gas, enclosed in the capacitance sensor shown in FIG. 2 and a case where it is enclosed in the form of liquid. The axis of abscissa of the graph stands for the contents of HFC32 and the axis of ordinate stands for the capacitance values which are the outputs from the capacitance sensor 3. As can be seen from FIG. 3, the liquid refrigerant exhibits larger capacitance values than the gaseous refrigerant. In particular, a large difference in the capacitance value arises between the gas and the liquid refrigerant HFC134a. It means a fact that change of the dryness of the refrigerant changes the capacitance value thereof. A comparison made between the capacitance value of HFC134a and that of HFC32 results in that HFC32 exhibits larger capacitance values regardless of the state of the refrigerant. It means a fact that only the gas or the liquid refrigerant is present in the capacitance sensor 3 and the change of the composition of the refrigerant changes the capacitance value. However, if an inside of the capacitance sensor 3 is brought into a gas-liquid phase, the capacitance value is changed due to the dryness of the refrigerant as well as the change of the composition of the mixed-refrigerant because of the foregoing characteristics, and therefore, the composition cannot be detected. Further, it is not possible to obtain a state where the liquid refrigerant is always present in the refrigerating cycle due to the operational state change. Therefore, when detecting the composition of the mixed-refrigerant by using the capacitance sensor 3, it must be located at a place in the refrigerating cycle where the mixed-refrigerant is present in the form of the gas (for example, in the pipe arranged from an outlet port of the compressor to an inlet port of the condenser).

Figure 4:
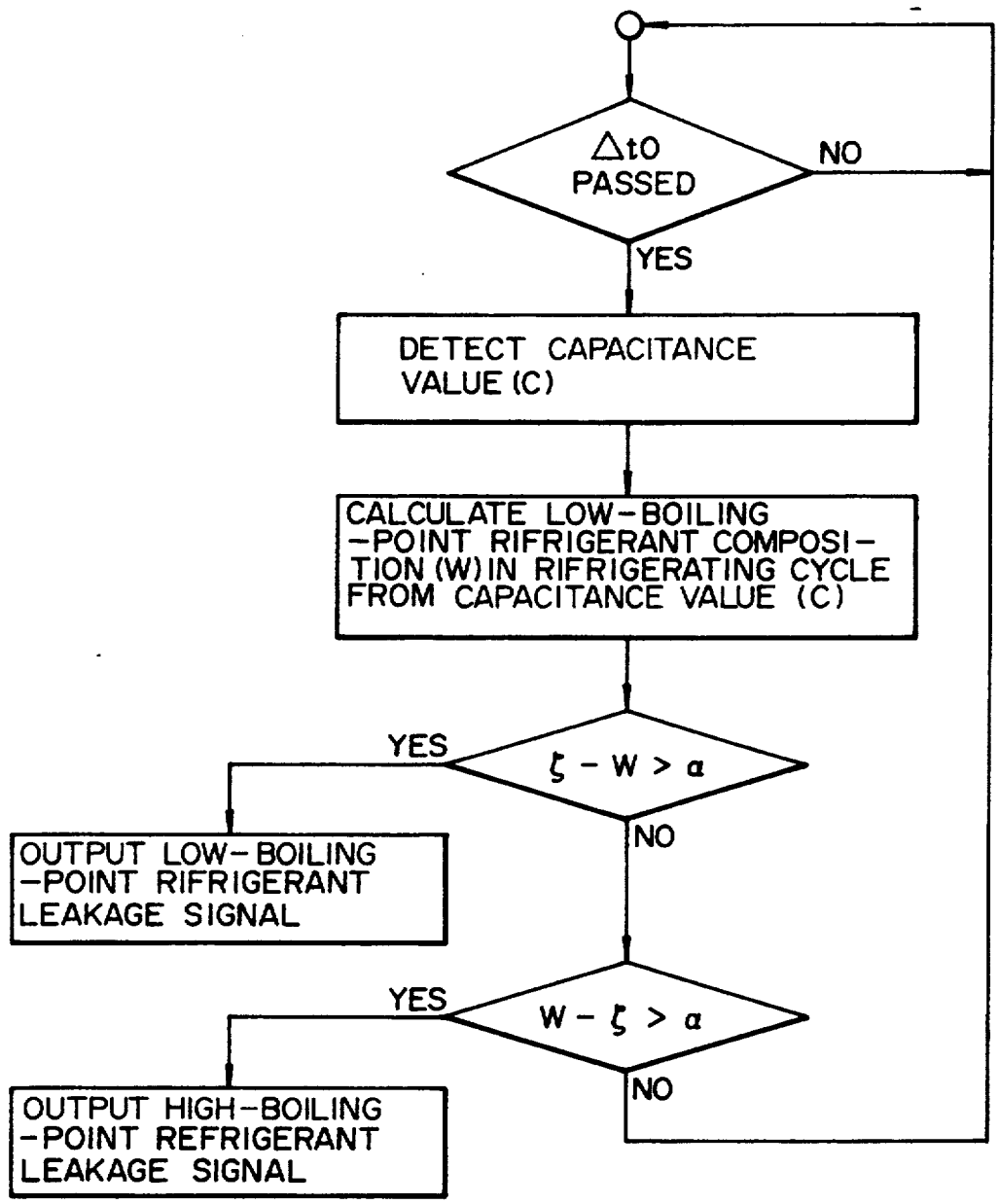
FIG. 4 is a flow chart of the procedure for detecting the refrigerant composition according to the first embodiment of the present invention.

A method for detecting the composition of the mixed-refrigerant circulating through the refrigerating cycle by making use of the capacitance sensor 3 will now be described with reference to FIGS. 1 and 4. FIG. 4 is a flow chart showing the method of detecting the composition of the mixed-refrigerant. At a moment at which a predetermined time period $\Delta t_0$ has passed, the capacitance sensor 3 detects capacitance value C of the gas refrigerant at the outlet port of the compressor through the capacitance detecting portion 11. The capacitance value C is input through the signal line to the refrigerant composition calculating portion 12. The refrigerant composition calculating portion 12 also receives an expression from the memory portion 13 which stores, in the form of the expression, the relationship between low-boiling-point refrigerant compositions W of the mixed-refrigerant and the capacitance values C as shown in FIG. 3. As a result, the refrigerant composition calculating portion 12 calculates the low-boiling-point refrigerant composition W of the mixed-refrigerant circulating through the refrigerating cycle. Further, a difference $\zeta - W$ between the initial composition value $\zeta$ of the enclosed refrigerant previously stored in the memory portion 15 and the calculated low-boiling-point refrigerant composition W of the mixed-refrigerant is calculated. If the difference $\zeta - W$ is larger than allowable change value $\alpha$ of the refrigerant composition, a judgement is made that the low-boiling-point refrigerant leaks out. Therefore, a signal denoting the leakage of the low-boiling-point refrigerant is output to cause the leakage of the low-boiling-point refrigerant to be recognized. Further, a difference $W - \zeta$ between the calculated low-boiling-point refrigerant composition W of the mixed-refrigerant and the initial composition value $\zeta$ of the enclosed refrigerant is calculated. If the difference $W - \zeta$ is larger than allowable change value $\alpha$ of the refrigerant composition, a judgement is made that the high-boiling-point refrigerant leaks out. Therefore, a signal denoting the leakage of the high-boiling-point refrigerant is output. The states except for the foregoing states are judged that the composition of the mixed-refrigerant circulating in the refrigerating cycle is in an adequate state, and, the detection of the composition of the mixed-refrigerant is repeated.

The refrigerant composition detecting method thus-constituted is arranged in such a manner that, even if the leakage of the refrigerant in the refrigerating cycle changes the composition of the refrigerant in the refrigerant circuit, the composition of the refrigerant in the refrigerant circuit is directly measured to judge whether or not the refrigerant composition is an adequate state. Therefore, the occurrence of abnormal refrigerant leakage can be easily and surely confirmed. By transmitting the output signal denoting the refrigerant leakage to a recognizing apparatus, such as a display lamp or a liquid crystal display portion, to cause the refrigerant leakage to be visual or audibly recognized, a necessity of removing all refrigerant from the refrigerant circuit at the time of supplement of the refrigerant can be eliminated. Since the supplement of the refrigerant is performed while confirming the refrigerant leakage recognizing apparatus, the refrigerant composition in the refrigerating cycle can be made surely and adequately. As a result, the maintenance time period can be shortened and the quantity of the needed refrigerant at the time of performing the maintenance can be reduced.

Although, in the above-embodiment, the relationship between the compositions of the mixed-refrigerant and the capacitance values has been considered while making the low-boiling-point refrigerant to be the standard, a similar effect can be obtained if the high-boiling-point refrigerant is made to be the standard. Although this embodiment is arranged in such a manner that the two-component% mixed-refrigerant is employed, a similar effect can be obtained also in a case where a multi-component mixed-refrigerant is used. Although the relationship between the capacitance values and the compositions of the mixed-refrigerant is considered by using HFC134a and HFC32, similar characteristics can be attained if other refrigerants are used. Therefore, the foregoing case is included within the scope of the present invention.

Figure 5:
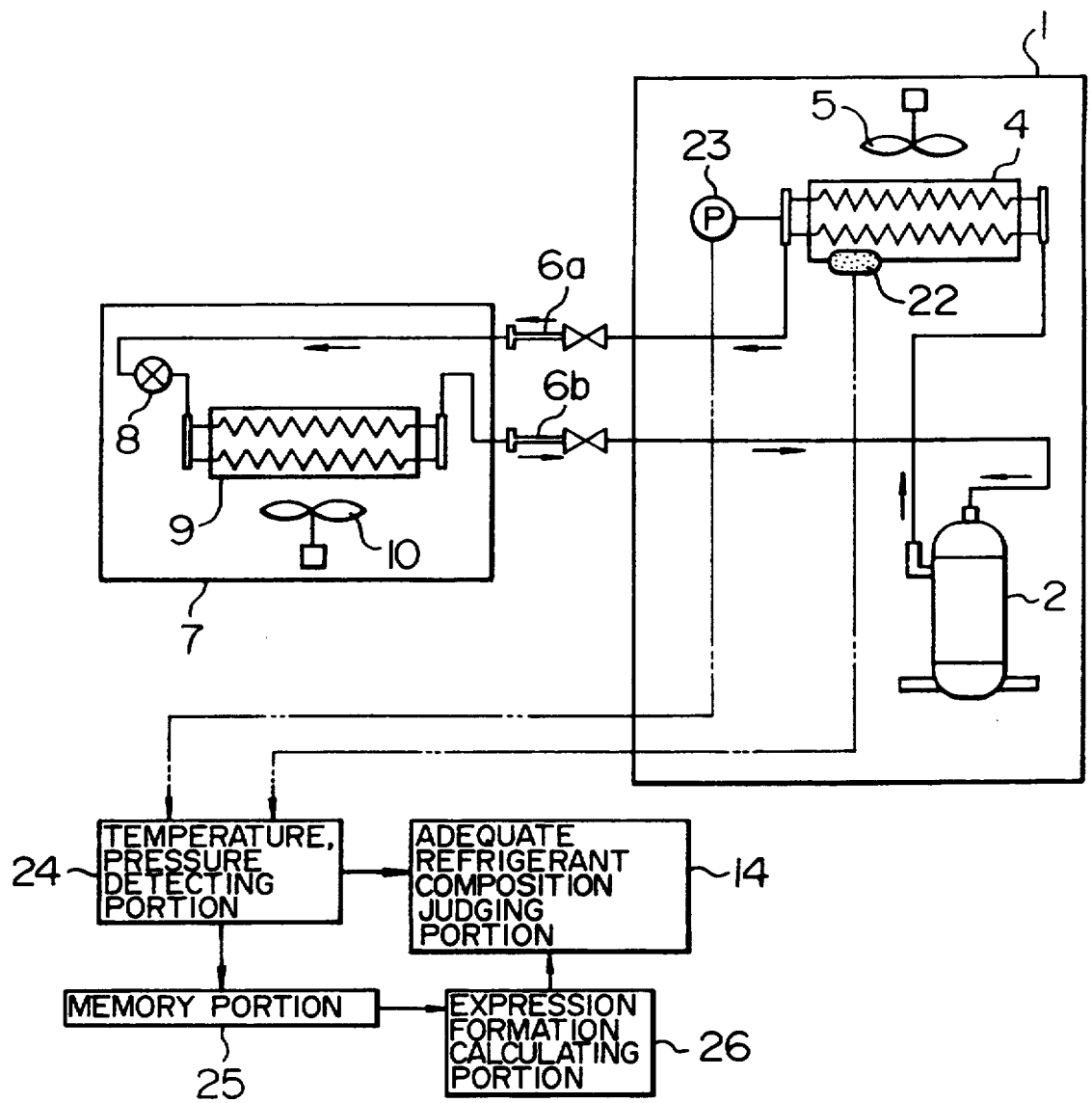
FIG. 5 is a structural view of a refrigerating cycle having adequate refrigerant composition detecting means arranged to use the temperature and the pressure according to a second embodiment of the refrigerant composition detection apparatus of the present invention.

FIG. 5 is a structural view which illustrates a refrigerating cycle having adequate refrigerant composition detecting means by means of the temperature and the pressure according to a second embodiment of the present invention. In FIG. 5, the same reference numerals as those shown in FIG. 1 represent the same elements. Referring to FIG. 5, the outdoor unit 1 has a temperature sensor 22 and a pressure sensor 23 for respectively detecting the condensation temperature and the condensation pressure in order to detect the composition of the mixed-refrigerant. Further, the composition value of the mixed-refrigerant to be detected by the temperature sensor 22 and the pressure sensor 23, realized when an adequate amount of mixed-refrigerant is enclosed, is memorized by a memory portion 25 provided for the outdoor unit 1. Further, an expression-formation calculating portion 26 for correcting and forming into an expression of the values of the temperature and the pressure to be stored in the memory potion 25 is provided for the outdoor unit 1. The temperature sensor 22, the pressure sensor 23, the memory portion 25 and the expression-formation calculating portion 26 are connected to one another by signal lines.

A principle of performing the judgement whether or not the composition of the mixed-refrigerant in the refrigerating cycle is adequate state by using the temperature sensor 22 and the pressure sensor 23 will now be described.

Figure 6:
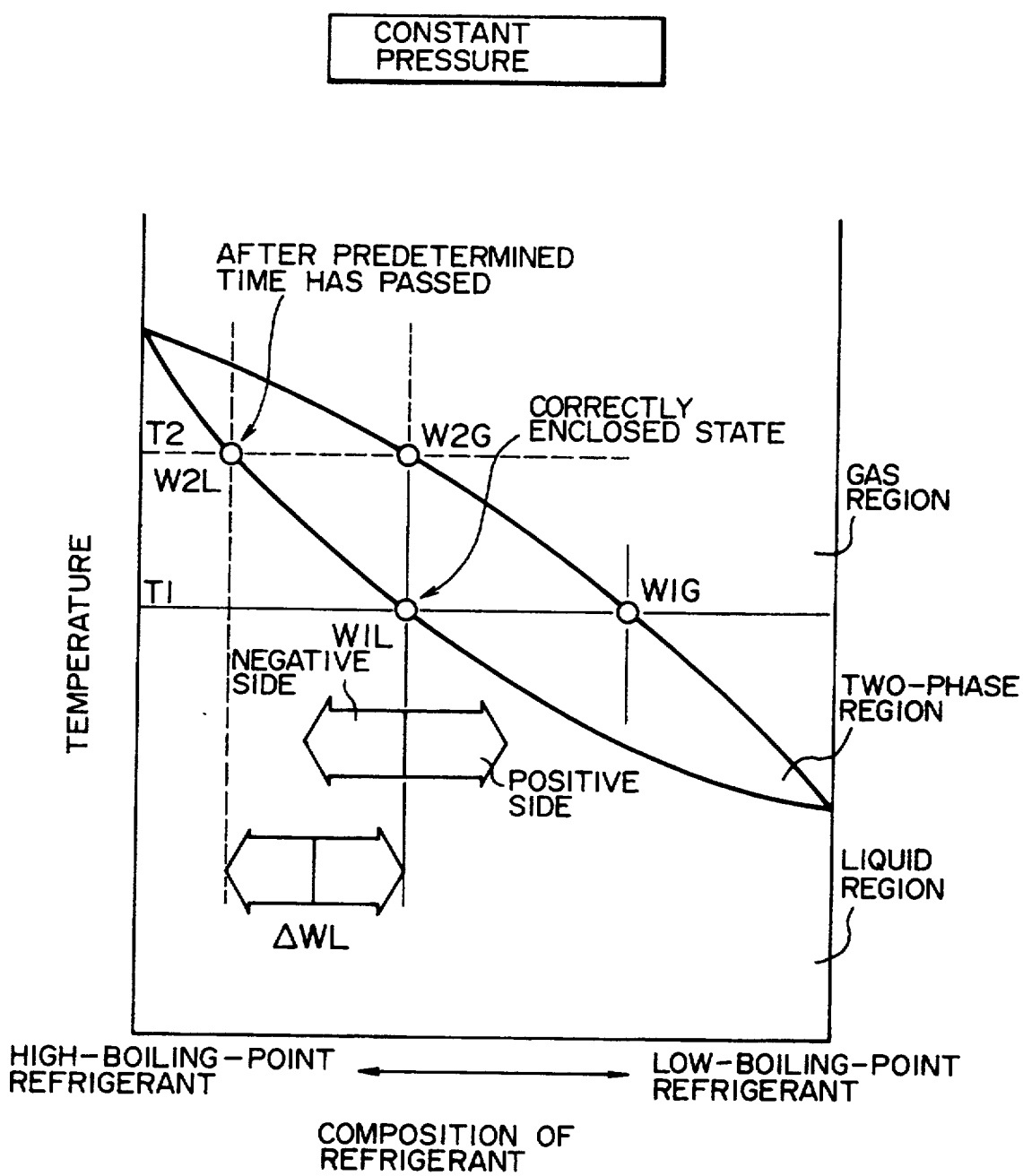
FIG. 6 is a gas-liquid equilibrium graph of the mixed-refrigerant.

FIG. 6 is a gas-liquid equilibrium graph of the mixed-refrigerant. FIG. 6 shows a relationship between the temperatures of the refrigerant and the compositions of the mixed-refrigerant under a predetermined constant pressure level. The axis of abscissa stands for the compositions, while axis of ordinate stands for the temperatures of the refrigerant. In FIG. 6, the upper line of the two lines is called a gas phase line and the lower line is called a liquid phase line. A portion above the gas phase line shows a gas region in which gas is solely present, a portion enclosed by the gas phase line and the liquid phase line shows a two-phase region in which the gas and liquid are present together, and a portion below the liquid phase line shows a liquid region in which liquid is solely present. The mixed-refrigerant has characteristics to present a certain temperature width when it is transformed from gas to liquid. Therefore, the composition of the mixed-refrigerant can be calculated by detecting the temperature and the pressure when the mixed-refrigerant is in a saturated gas state or saturated liquid state. However, it is difficult to detect always the temperature and the pressure of the mixed-refrigerant in the saturated state in the refrigerating cycle because the operational state always varies and there are occurrence of leakage of the refrigerant and retention of the refrigerant. However, the temperature and the pressure of the mixed-refrigerant in the two-phase state can be easily detected. Accordingly, the temperature sensor 22 and the pressure sensor 23 are, as shown in FIG. 5, provided for the purpose of detecting the condensation temperature and the condensation pressure of the refrigerant in the refrigerating cycle in such a manner that condensation temperature T1 and condensation pressure P are detected by the corresponding sensors when the mixed-refrigerant is enclosed correctly. In the gas-liquid equilibrium graph of the mixed-refrigerant shown in FIG. 6, at the temperature T1, the compositions of the mixed-refrigerant in the form of the saturated gas and in the form of the saturated liquid are W1L and W1G, respectively. Since the temperature sensor 22 and the pressure sensor 23 are so disposed that the state of the two-phase region in the refrigerating cycle can be measured, it is a certain fact that the composition of the mixed-refrigerant which is enclosed adequately in the refrigerating cycle is present between the refrigerant composition W1B of the saturated gas and the refrigerant composition W1L of the saturated liquid. After a predetermined time has passed, condensation temperature T2 and condensation pressure P are detected similarly to the case where the mixed-refrigerant is enclosed adequately, resulting in that the compositions of the mixed-refrigerant in the form of the saturated gas and in the form of the saturated liquid are W2G and W2L respectively as shown in the gas-liquid equilibrium graph of the mixed-refrigerant shown in FIG. 6. It is a certain fact that the composition of the mixed-refrigerant in the refrigerating cycle is, similarly to the foregoing case, present between the refrigerant composition W2G of the saturated gas and the refrigerant composition W2L of the saturated liquid. Noting the refrigerant compositions W1L and W2B, the refrigerant composition W1l of the saturated liquid in the state where the mixed-refrigerant is enclosed adequately is a lower limit of the refrigerant composition and the refrigerant composition W2G of the saturated gas after the predetermined time has passed is an upper limit of the refrigerant composition. That is, the state where the refrigerant composition W2G of the saturated gas after the predetermined time has passed is lowered than the refrigerant composition W1L of the saturated liquid in the state where the mixed-refrigerant is enclosed adequately is a state where the refrigerant composition in the refrigerating cycle has been changed certainly. Therefore, when it is judged whether or not the temperature is higher or lower than the level with which the foregoing state is realized, it is possible to judge the leak age of the refrigerant. However, it is very difficult to realize the same pressure during the operation of the refrigerating cycle because the operational state always differs. Accordingly, the temperatures in the state where the refrigerant is enclosed adequately under various pressure conditions are formed into expression to be memorized. As a result, the refrigerant composition can be detected regardless of the state of the operation.

Figure 7:
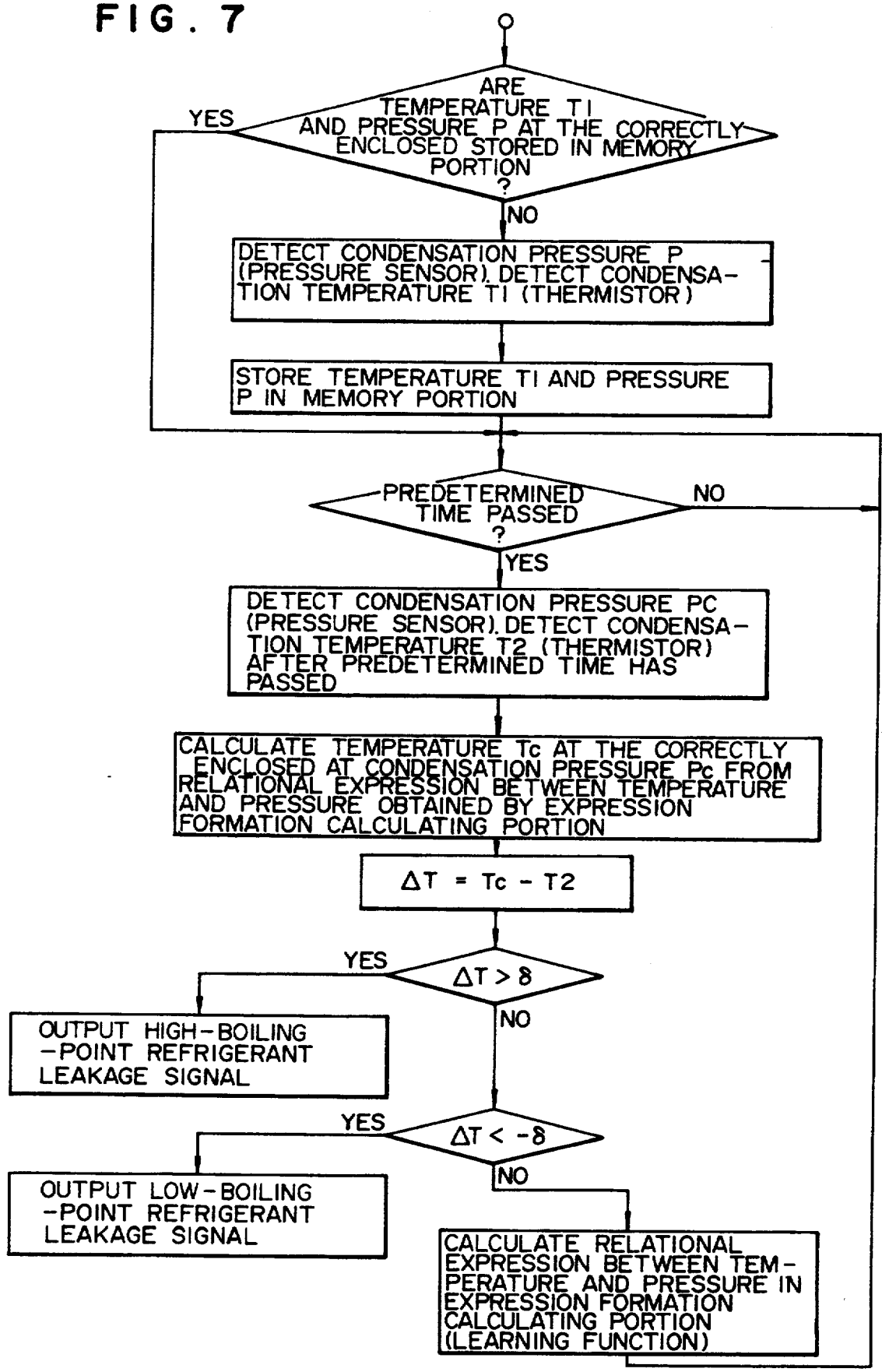
FIG. 7 is a flow chart of detection and control of an adequate refrigerant composition by means of the temperature and the pressure. according to the second embodiment of the present invention.

The method of detecting the composition of the mixed-refrigerant in the refrigerating cycle according to the second embodiment will now be described with reference to FIGS. 5 and 7. FIG. 7 is a flow chart of the method of detecting the composition of the refrigerant by means of the temperature and the pressure. First, a judgement is made whether or not the temperature and the pressure at the time when it is correctly enclosed have been memorized in the memory portion 25. If the temperature and the pressure have not been memorized (for example, in a state immediate after installation), the condensation temperature T1 and the condensation pressure P are detected by the corresponding temperature sensor 22 and the pressure sensor 23. The results of the detection are memorized in the memory portion 25. After a predetermined time has passed, the condensation temperature T2 and the condensation pressure Pc are detected by the corresponding temperature sensor 22 and the pressure sensor 23. Then, temperature Tc at the correctly enclosed corresponding to the pressure Pc is calculated. A difference $\Delta T$ ($\Delta T = Tc - T2$) between the temperature Tc at correctly enclosed and value T2 detected by the temperature sensor is calculated. The temperature difference $\Delta T$ and a predetermined value $\delta$ (for example, 6° C.) are compared. If the temperature difference $\Delta T$ is larger than the value $\delta$, it is judged that the high-boiling-point refrigerant has leaked out, and a signal denoting the leakage of the high-boiling-point refrigerant is output. Also, the temperature difference $\Delta T$ and the predetermined value-$\delta$ are compared. If the temperature difference $\Delta T$ is smaller than the predetermined value-$\delta$, it is judged that low-boiling-point refrigerant has leaked out, and a signal denoting the leakage of the low-boiling-point refrigerant is output. The cases except for the foregoing cases are judged that the composition of the mixed-refrigerant circulating in the refrigerating cycle is in the adequate state. Then, the value T2 detected by the temperature sensor is input to the expression-formation calculating portion and the relational expression between the temperature and the pressure is learned. The detection of the composition of the mixed-refrigerant is repeated.

Since the refrigerant composition detecting method thus-constituted is arranged in such a manner that the temperature detecting means and the pressure detecting means already provided for the conventional refrigerating cycle are used to judge whether or not the composition of the mixed-refrigerant circulating the refrigerating cycle is in an adequate state, the abnormal refrigerant leakage can be easily and surely confirmed. By supplying the output signal denoting the refrigerant leakage to the recognizing device such as the display lamp or the liquid crystal display to enable the refrigerant leakage to be recognized visually or audibly, a necessity of removing all refrigerant from the refrigerant circuit at the time of supplement of the refrigerant can be eliminated. Since the supplement of the refrigerant is performed while confirming the refrigerant leakage recognizing apparatus, the refrigerant composition in the refrigerating cycle can be made adequately. As a result, the maintenance time period can be shortened and the quantity of the needed refrigerant at the time of performing the maintenance can be reduced. Further, the arrangement that the detecting means already provided for the conventional refrigerating cycle is used to detect the composition enables the sensor serving as the composition detecting means to be omitted from the structure. As a result, the cost can be reduced and the control circuit can be formed simply.

Although this embodiment has the arrangement that the temperature sensor 22 and the pressure sensor 23 are disposed in the condensing-side heat-exchanger, they may be disposed in the evaporating-side heat-exchanger to obtain a similar effect.

Figure 8:
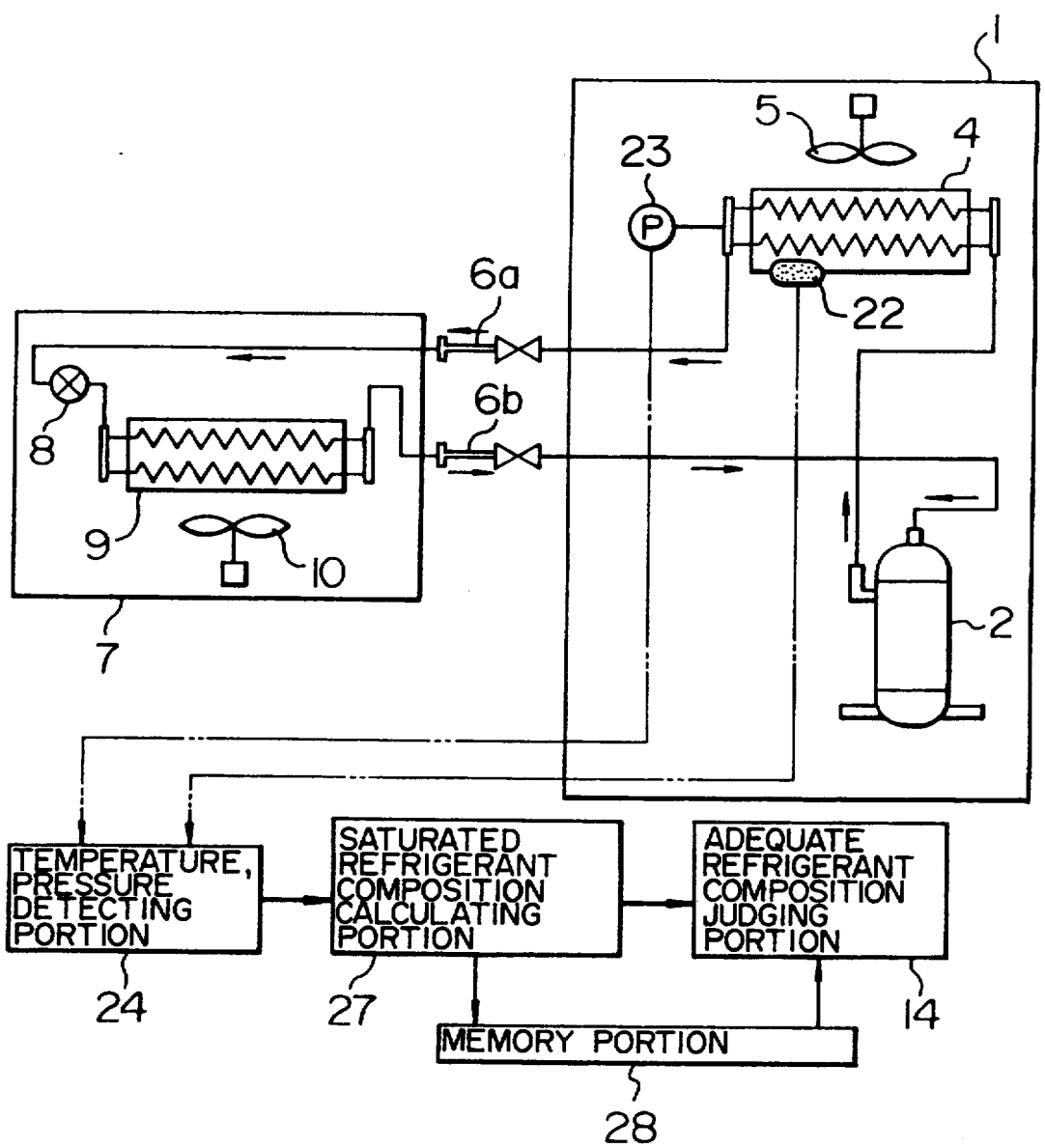
FIG. 8 is a structural view of a refrigerating cycle having saturated refrigerant composition detecting means arranged to use the temperature and the pressure according to a third embodiment of the refrigerant composition detecting apparatus of the present invention.

A third embodiment of the present invention will now be described with reference to FIG. 8. FIG. 8 is a structural view of a refrigerating cycle having saturated refrigerant composition detecting means by means of the temperature and the pressure. In FIG. 8, the same reference numerals as those shown in FIGS. 1 and 5 represent the same elements. As shown in FIG. 8, the outdoor unit 1 comprises a temperature and pressure detecting portion 24 for detecting the temperature and the pressure of the mixed-refrigerant and an adequate refrigerant composition judging portion 14 for judging whether or not the refrigerant composition is in an adequate state. Further, a saturated refrigerant composition calculating portion 27 for calculating the refrigerant composition realized in the saturated state from the temperature and the pressure in the gas-liquid phase, and a memory portion 28 for storing the saturated refrigerant composition value realized at the time when the refrigerant is enclosed disposed between the temperature and pressure detecting portion 24 and the adequate refrigerant composition judging portion 13.

A principle of judging whether or not the composition of the mixed-refrigerant in the refrigerating cycle is in the adequate skate will now be described. Referring to FIG. 6, refrigerant compositions W1L and W2L of the respective saturated fluids calculated from the temperature and the pressure in the gas-liquid state at correctly enclosed and after the predetermined time has passed are paid attention. As a result, composition change width DW which is a difference between the refrigerant composition W2L after the predetermined time has passed and the refrigerant composition W1L of the saturated liquid at the time of correctly enclosed is the result of the change of the refrigerant composition in the refrigerating cycle occurring due to the leakage of the refrigerant. Therefore, it is necessary to enable the leakage of the refrigerant to be recognized if the composition change width $\Delta W$ is larger than a certain value. A fact that the composition change width $\Delta W$ is brought to positive values means a fact that the composition of the mixed-refrigerant in the refrigerating cycle has been deflected to the low-boiling-point side. Therefore, the foregoing fact means that the high-boiling-point has leaked out. A fact that the composition change width $\Delta W$ is brought to negative values means a fact that the composition of the mixed-refrigerant in the refrigerating cycle has been deflected to the high-boiling-point side. Therefore, the foregoing fact means that the low-boiling-point has leaked out. As a result, with the foregoing method, it is possible to detect which kind of the refrigerant has leaked out.

Figure 9:
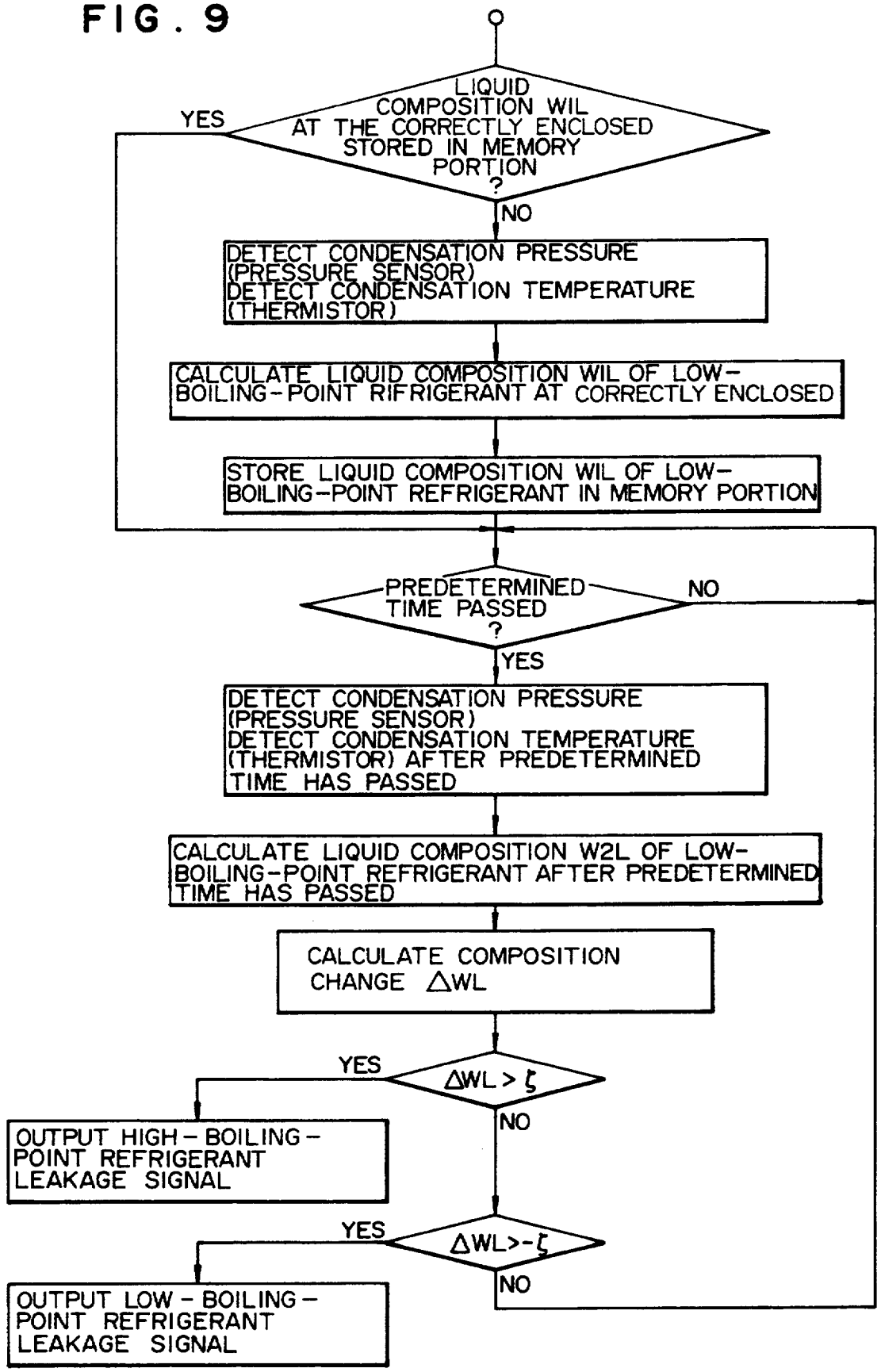
FIG. 9 is a flow chart of detection and control of the saturated refrigerant by means of the temperature and the pressure according to the embodiment shown in FIG. 8.

The third embodiment of the present invention will now be described with reference to FIGS. 8 and 9. FIG. 9 is a flow chart which explains the method of detecting the composition of the mixed-refrigerant by using the saturated refrigerant composition detecting means by means of the temperature and the pressure. First, it is judged whether or not the refrigerant composition W1L of the saturated liquid at the time of the adequately enclosed has been stored in the memory portion 28. If the refrigerant composition W1L of the saturated liquid is not stored (for example, in a state just after installation), the condensation temperature and the condensation pressure are detected by the corresponding temperature sensor 22 and the pressure sensor 23. Then, the gas-liquid equilibrium graph of the mixed-refrigerant as shown in FIG. 6 is stored in the memory portion 28. Further, the liquid composition W1L of the low-boiling-point refrigerant at the time of the adequately enclosed is calculated and the results of the calculation is stored in the memory portion 28. After a predetermined time has passed, the condensation temperature and the condensation pressure are detected by the corresponding temperature sensor 22 and the pressure sensor 23. Then, the liquid composition W2L of the low-boiling-point refrigerant after the predetermined time has passed is calculated. Then, a calculation is performed to obtain composition change width $\Delta WL$ ($\Delta WL = W2L - W1L$) which is the difference between the liquid composition W2L of the low-boiling-point refrigerant after the predetermined time has passed and the liquid composition W1L of the low-boiling-point refrigerant at the adequately enclosed stored in the memory portion 28, the obtained composition change width $\Delta$WL and predetermined value $\zeta$ (for example, 0.1) are compared. If the composition change width $\Delta$WL is larger than the predetermined value $\zeta$, it is judged that the high-boiling-point refrigerant has leaked out, and a signal denoting the leakage of the high-boiling-point refrigerant is output. Also, the composition change width $\Delta$WL and predetermined value-$\zeta$ are compared. If the composition change width $\Delta$WL is smaller than the predetermined value-$\delta$, it is judged that low-boiling-point refrigerant has leaked out, and a signal denoting the leakage of the low-boiling-point refrigerant is output. The cases except for the foregoing cases are judged that the composition of the mixed-refrigerant circulating in the refrigerating cycle is in the adequate state. Then, the foregoing composition detection of the mixed-refrigerant is repeated.

Since the refrigerant composition detecting method thus-constituted is arranged in such a manner that the temperature detecting means and the pressure detecting means already provided for the conventional refrigerating cycle are used to judged whether or not the composition of the mixed-refrigerant circulating the refrigerating cycle is in an adequate state, the abnormal refrigerant leakage can be easily and surely confirmed. By supplying the output signal denoting the refrigerant leakage to the recognizing device such as the display lamp or the liquid crystal display to enable the refrigerant leakage to be recognized visually or audibly, a necessity of removing all refrigerant from the refrigerant circuit at the time of supplement of the refrigerant can be eliminated. Since the supplement of the refrigerant is performed while confirming the refrigerant leakage recognizing apparatus, the refrigerant composition in the refrigerating cycle can be made adequately. As a result, the maintenance time period can be shortened and the quantity of the needed refrigerant at the time of performing the maintenance can be reduced. Further, the arrangement that the detecting means already provided for the conventional refrigerating cycle is used to detect the composition enables the sensor serving as the composition detecting means to be omitted from the structure. As a result, the cost can be reduced and the control circuit can be formed simply.

Although the detection of the composition of the mixed-refrigerant is performed while making the low-boiling-point refrigerant to be the standard, a similar effect can be obtained when the high-boiling-point refrigerant is considered to be the standard. Further, the composition value of the saturated liquid employed in this embodiment may be replaced by the composition value of the saturated gas as the standard to obtain a similar effect. In addition, combination of the composition value of the mixed-refrigerant in the form of the saturated gas and the composition value of the mixed-refrigerant in the form of the saturated liquid may be employed to obtain a similar effect. Although this embodiment has the arrangement that the temperature sensor 22 and the pressure sensor 23 are disposed in the condensing-side heat exchanger, they may be disposed in the evaporating-side heat-exchanger to obtain a similar effect.

Figure 10:
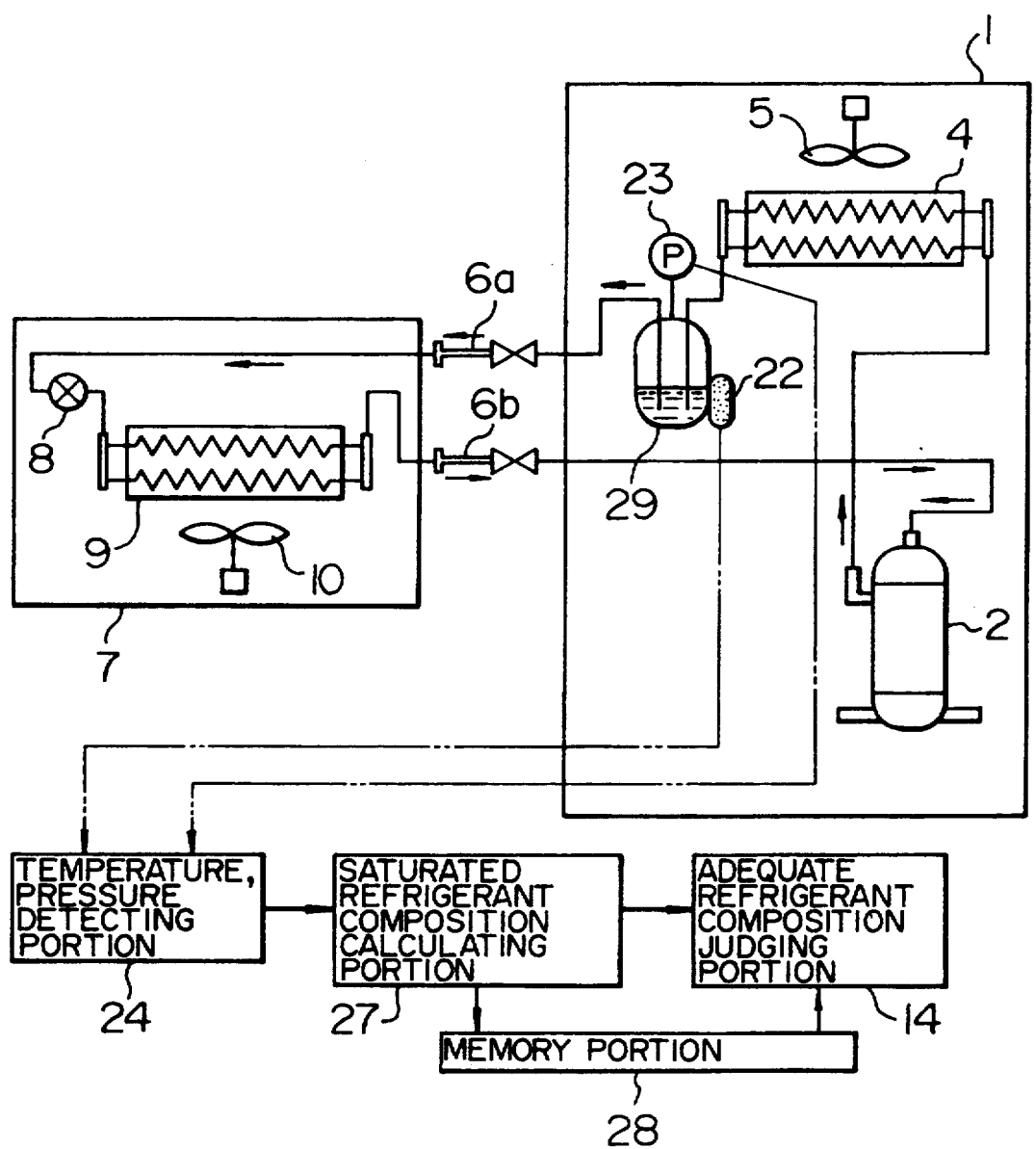
FIG. 10 is a structural view of a refrigerating cycle having saturated refrigerant composition detecting means arranged to use the temperature and the pressure of a liquid receptor according to a fourth embodiment of a refrigerant composition detecting apparatus according to the present invention.

A fourth embodiment of the present invention will now be described with reference to FIG. 10. FIG. 10 is a structural view which illustrates a refrigerating cycle having saturated refrigerant composition detecting means by means of the temperature and the pressure in a liquid receptor. In FIG. 10, the same reference numerals as those shown in FIGS. 1 and 8 represent the same elements. Referring to FIG. 10, a liquid receptor 29 for reserving an excessive refrigerant is disposed at an outlet port of the condensing-side heat exchanger 4. Further, the temperature sensor 22 and the pressure sensor 23 for detecting the composition of the refrigerant are disposed so as to measure the state in the liquid receptor 29.

A principle to judge whether or not the composition of the mixed-refrigerant in the refrigerating cycle will now be described. As described in the third and fourth embodiments, the calculation of the saturated refrigerant composition from the detected temperature and pressure in the two phase region to compare with the saturated refrigerant composition value at the time of the enclosure of the refrigerant makes it possible to judge whether or not the refrigerant composition in the refrigerating cycle is in an adequate state. An inside portion of the liquid receptor 29 disposed at the outlet port of the condensing-side heat-exchanger 4 is brought into substantially a gas-liquid phase in which the saturated liquid and the saturated gas are present together, such as the two phase region surrounded by the gas phase line and the liquid phase line shown in FIG. 6. Therefore, the present embodiment is arranged in such a manner that the temperature sensor 22 and the pressure sensor 23 are disposed to detect the temperature and the pressure in the liquid receptor 29. Therefore, it is possible to judge whether or not the refrigerant composition is adequate.

Since the method of detecting the refrigerant composition according to this embodiment is the same as that according to the third embodiment, its description is omitted here.

Since the refrigerant composition detecting apparatus thus-constituted is arranged in such a manner that the temperature and the pressure of the liquid receptor, which is brought into the gas-liquid phase, are used to judge whether or not the composition of the mixed-refrigerant circulating in the refrigerating cycle is in the adequate state, the occurrence of abnormal refrigerant leakage can be easily confirmed. By transmitting the output signal denoting the refrigerant leakage to a recognizing apparatus such as a display lamp or a liquid crystal display to enable the refrigerant leakage to be visual or audibly recognized, a necessity of removing all refrigerant from the refrigerant circuit at the time of supplement of the refrigerant can be eliminated. Since the supplement of the refrigerant is performed while confirming the refrigerant leakage recognizing apparatus, the refrigerant composition in the refrigerating cycle can be made adequately. As a result, the maintenance time period can be shortened and the quantity of the needed refrigerant at the time of performing the maintenance can be reduced. Further, the composition is detected by using the detecting means already provided for the conventional refrigerating cycle. Therefore, the sensor serving as the composition detecting means can be omitted from the structure. As a result, the cost can be reduced and the control circuit can be simplified.

Figure 11:
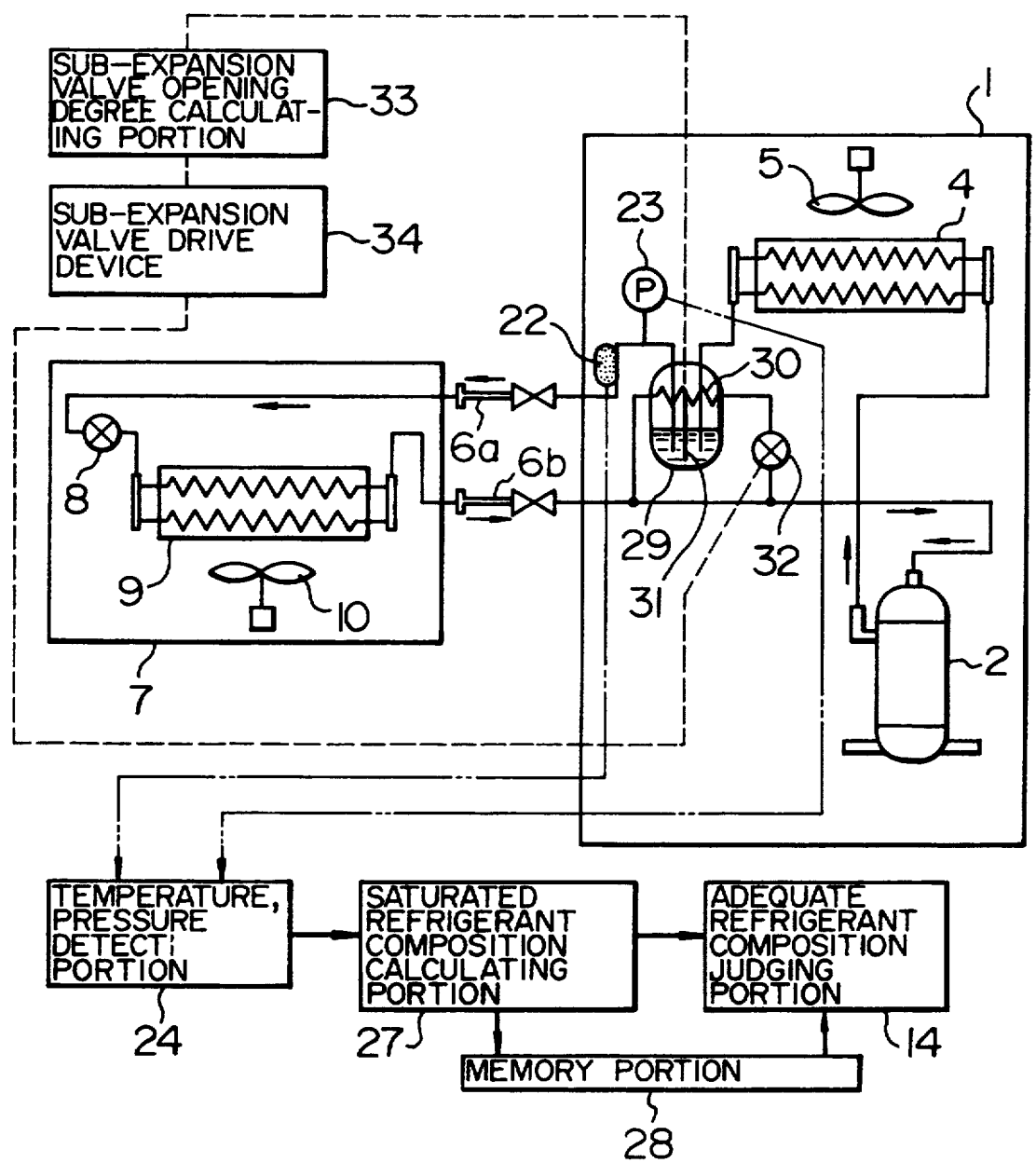
FIG. 11 is a structural view of a refrigerating cycle having saturated refrigerant composition detecting means according to a fifth embodiment of a refrigerant composition detecting apparatus according to the present invention.

A fifth embodiment of the present invention will now be described with reference to FIG. 11. FIG. 11 is a structural view which illustrates a refrigerating cycle having saturated liquid refrigerant composition detecting means. In FIG. 11, the same reference numerals as those shown in FIGS. 1, 8 and 10 represent the same elements. Referring to FIG. 11, the liquid receptor 29 includes a liquid-level detecting sensor 31 (for example, a capacitance sensor) capable of detecting a liquid level in the liquid receptor 29. In order to adjust the liquid level in the liquid receptor 29, this embodiment comprises a bypass passage between the outlet port of the evaporating-side heat-exchanger 9 to an inlet port of the compressor 2. Further, the bypass passage has a liquid-receptor cooling device 30 (for example, a heat-exchanger) for cooling the liquid receptor 29 and a subexpansion valve 32 capable of adjusting the flow rate of the refrigerant passing through the liquid-receptor cooling device 30 for the purpose of adjusting the cooling performance of the liquid-receptor cooling device 30. A sub-expansion valve opening degree calculating portion 33 for calculating the degree of opening of the sub-expansion valve 32 and a sub-expansion valve drive device 34 for driving the sub-expansion valve 32 in response to an output signal from the sub-expansion valve opening degree calculating portion 33 are, by signal lines, connected to the sub-expansion valve 32 in order to make the liquid level in the liquid receptor 29 to be constant in response to the output signal from the liquid level detecting sensor 31.

A principle to detect the composition of the mixed-refrigerant in the refrigerating cycle will now be described. Since the refrigerant in the liquid receptor 29 is substantially in the saturated state as described above, the refrigerant substantially in the form of the saturated liquid flows at the outlet port of the liquid receptor 29 as long as the liquid is present in the liquid receptor 29. That is, the refrigerant circulating in the refrigerating cycle is in the state of the composition of the saturated liquid. Therefore, the composition of the mixed-refrigerant can be obtained by using the temperature sensor 22 and the pressure sensor 23 disposed at the outlet port of the liquid receptor 29 to detect the temperature and the pressure to calculate the composition of the refrigerant designated by the liquid phase line from the relationship among the refrigerant composition, the temperature and the pressure shown in FIG. 6.

Since the method of detecting the composition of the refrigerant by using the refrigerant composition detecting means according to the present invention is the same as that according to the third embodiment, its description is omitted here Since the refrigerant composition detecting method thus-constituted is arranged in such a manner that the temperature and the pressure at the outlet port of the liquid receptor, which is brought into the saturated liquid state, are used to judge whether or not the composition of the mixed-refrigerant circulating in the refrigerating cycle is in the adequate state, the occurrence of abnormal refrigerant leakage can be easily be confirmed. By transmitting the output signal denoting the refrigerant leakage to a recognizing apparatus such as a display lamp or a liquid crystal display, to cause the refrigerant leakage to be visual or audibly recognized, a necessity of removing all refrigerant from the refrigerant circuit at the time of supplement of the refrigerant can be eliminated. Since the supplement of the refrigerant is performed while confirming the refrigerant leakage recognizing apparatus, the refrigerant composition in the refrigerating cycle can be made surely. As a result, the maintenance time period can be shortened and the quantity of the needed refrigerant at the time of performing the maintenance can be reduced. Further, the composition is detected by using the detecting means already provided for the conventional refrigerating cycle. Therefore, the sensor serving as the composition detecting means can be omitted from the structure. As a result, the cost can be reduced and the control circuit can be simplified. Since the liquid level in the liquid receptor 29 is adjusted by using the liquid receptor cooling device 30 and the subexpansion valve 32, the change of the composition of the refrigerant circulating in the refrigerating cycle taken place due to the change of the liquid level in the liquid receptor 29 can be prevented and it becomes possible to make the operation of the refrigerating cycle stable. Further, common use of the output signal denoting the liquid level in the liquid receptor 29 and that denoting the refrigerant composition enables the additional quantity of the enclosure refrigerant to be calculated.

Figure 12:
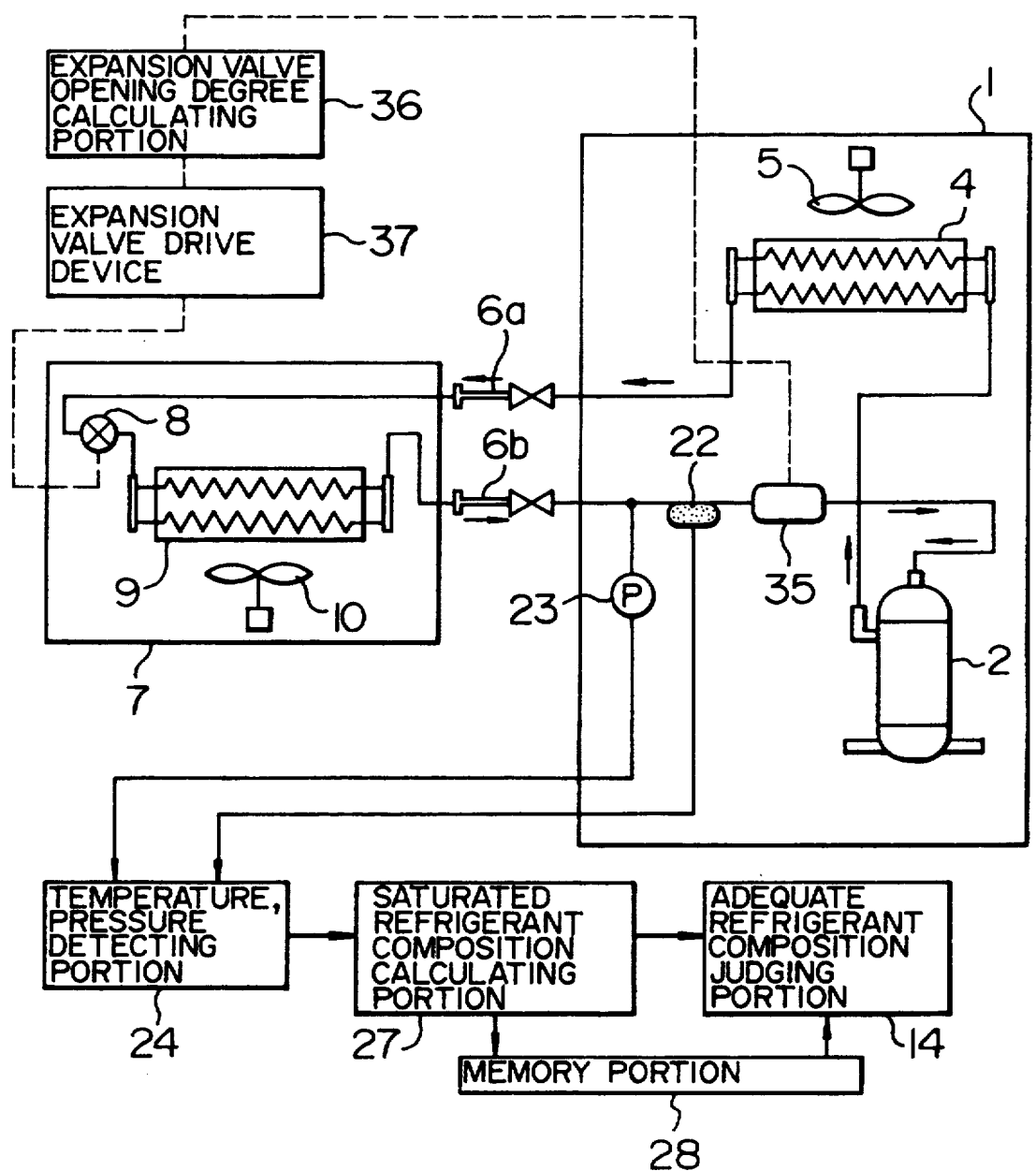
FIG. 12 is a structural view of a refrigerating cycle having saturated gas refrigerant composition detecting means arranged to use the temperature and the pressure according to a sixth embodiment of a refrigerant composition detecting apparatus of the present invention.

A sixth embodiment of the present invention will now be described with reference to FIG. 12. FIG. 12 is a structural view which illustrates a refrigerating cycle having saturated liquid refrigerant composition detecting means. In FIG. 12, the same reference numerals as those shown in FIGS. 1 and 8 represent the same elements. Referring to FIG. 12, a wetness sensor 35 (for example, a capacitance sensor) capable of detecting the wetness of the refrigerant is disposed in a pipe arranged from the outlet port of the evaporating-side heat-exchanger 9 to the inlet port of the compressor 2. The expansion valve 8 has, connected thereto via signal lines, an expansion valve opening degree calculating portion 36 for calculating the degree of opening of the expansion valve 8 and an expansion valve drive device 37 for driving the expansion valve 8 in response to an output signal from the expansion valve opening degree calculating portion 36 in order to adjust the wetness of the refrigerant flowing through the pipe arranged from the outlet port of the evaporating-side heat-exchanger 9 to the inlet port of the compressor 2.

A principle to detect the composition of the mixed-refrigerant in the refrigerating cycle will now be described. The refrigerant flowing through the pipe arranged from the outlet port of the evaporating-side heat-exchanger 9 to the inlet port of the compressor 2 is positively brought into a gas-liquid phase or substantially saturated gas state because the expansion valve 8 is driven in accordance with the output signal from the wetness sensor 35. In the case of the gas-liquid phase in FIG. 6, paying attention to the refrigerant compositions W1G and W2G of the saturated gases in the respective adequately enclosed state and the state after the predetermined time has passed and calculated from the temperature and the pressure in the gas-liquid state results in a knowledge to be obtained that the composition change width $\Delta W$, which is a difference between the refrigerant composition W2G of the saturated gas after the predetermined time has passed and the refrigerant composition W1G of the saturated gas in the adequately enclosed state, is a changed value of the refrigerant composition in the refrigerating cycle due to leakage of the refrigerant. Therefore, it is possible to recognize the leakage of the refrigerant when the composition change width $\Delta W$ is larger than a certain value. The fact that the composition change width $\Delta W$ is brought into positive values means a fact that the composition of the mixed-refrigerant in the refrigerating cycle has been brought into the low-boiling-point side. Therefore, it means a fact that the high-boiling-point refrigerant has leaked. The fact that the composition change width ΔW is brought into negative values means a fact that the composition of the mixed-refrigerant in the refrigerating cycle has been brought into the high-boiling-point side. Therefore, it means a fact that the low-boiling-point refrigerant has leaked. As a result, the type of the refrigerant allowed to leak can be detected. In the case where the substantially saturated gas state is realized, the substantially saturated gaseous refrigerant flows through the pipe from the outlet port of the evaporating-side heat-exchanger 9 to the inlet port of the compressor 2. That is, the saturated gas refrigerant circulates in the refrigerating cycle. Therefore, the composition can be obtained by detecting the temperature and the pressure by using the temperature sensor 22 and the pressure sensor 23 disposed between the outlet port of the evaporating-side heat-exchanger 9 and the inlet port of the compressor 2 to calculate the refrigerant composition designated by the gas phase line in accordance with the relationship among the refrigerant composition, the temperature and the pressure shown in FIG. 6.

Since the method of detecting the composition of the refrigerant by using the refrigerant composition detecting means according to the present invention is the same as that according to the third embodiment, its description is omitted here.

Since the refrigerant compositing detection method thus-constituted is arranged in such a manner that the temperature and the pressure of the pipe arranged from the outlet port of the evaporating-side heat-exchanger 9 to the inlet port of the compressor 2, which is brought into the saturated gas state, are used to judge whether or not the composition of the mixed-refrigerant circulating in the refrigerating cycle is in an adequate state, the occurrence of abnormal refrigerant leakage can be easily confirmed. By transmitting the output signal denoting the refrigerant leakage to a recognizing apparatus such as a display lamp or a liquid crystal display to cause the refrigerant leakage to be visual or audibly recognized, a necessity of removing all refrigerant from the refrigerant circuit at the time of supplement of the refrigerant can be eliminated. Since the supplement of the refrigerant is performed while confirming the refrigerant leakage recognizing apparatus, the refrigerant composition in the refrigerating cycle can be made surely. As a result, the maintenance time period can be shortened and the quantity of the needed refrigerant at the time of performing the maintenance can be reduced. Further, the composition is detected by using the detecting means already provided for the conventional refrigerating cycle. Therefore, the sensor serving as the composition detecting means can be omitted from the structure. As a result, the cost can be reduced and the control circuit can be simplified. Since the temperature and pressure detecting means for detecting the refrigerant composition can also be used to control the operation of the refrigerating cycle, the number of the sensor devices can be decreased.

We claim:

1. A refrigerant composition detecting apparatus having a mixed-refrigerant comprising a high-boiling-point refrigerant and a low-boiling-point refrigerant enclosed in a refrigerating cycle having a compressor, a condenser, a pressure reducing device and an evaporator, wherein said apparatus comprising:

temperature detecting means and pressure detecting means disposed in a gas-liquid phase portion of said refrigerating cycle;

saturated refrigerant composition judging means for judging the composition of said mixed-refrigerant in a saturated condition circulating in said refrigerating cycle in accordance with output signals from said temperature detecting means and said pressure detecting means;

memory means for storing an output signal from said saturated refrigerant composition judging means at a time when said refrigerant is correctly enclosed in the cycle;

composition-change calculating means for calculating a difference between a composition value realized after a predetermined time has passed and obtained by said saturated refrigerant composition judging means and a composition value stored in said memory portion and realized at the time of correctly enclosed; and adequate composition judging means for judging whether or not the composition of said mixed-refrigerant circulating in said refrigerating cycle is in an adequate state in accordance with an output signal from said composition change calculating means.

2. A refrigerant composition detecting apparatus according to claim 1 further comprising expression formation calculating means for storing and forming into an expression of said output signals from said temperature detecting means and said pressure detecting means at the time of adequately enclosed.

* * * * *